(«ф) United States Patent [19] [11] Patent Number: 4,968,248
McColgan et al. [45] Date of Patent: Nov. 6, 1990

[54] INTERDENTAL IMMOBILIZATION DEVICE

[75] Inventors: Colin McColgan, Komoka; Boris O. Divis, Campbell River, both of Canada

[73] Assignee: Dimac Medical Limited Partnership, Campbell River, Canada

[21] Appl. No.: 338,935

[22] Filed: Apr. 12, 1989

[30] Foreign Application Priority Data

Sep. 27, 1988 [CA] Canada ................................. 578613
Feb. 28, 1989 [CA] Canada ................................. 592368

[51] Int. Cl.⁵ ............................................. A61C 3/00
[52] U.S. Cl. ..................................... 433/18; 128/89 A
[58] Field of Search ......................... 433/18, 215, 19; 128/89 A

[56] References Cited

U.S. PATENT DOCUMENTS 2,481,177  9/1949  Tofflemire .................. 128/89 A
2,502,902  4/1950  Tofflemire .................. 128/89 A
4,202,328  5/1980  Sukkarie .................... 128/89 A
4,727,867  3/1988  Knoderer ................... 128/136
4,813,869  3/1989  Gatewood ..................... 423/18

Primary Examiner—Cary E. Stone
Attorney, Agent, or Firm—Mitches & Co.

[57] ABSTRACT

An interdental immobilization device consists, in the preferred embodiment, of a longitudinal deformable shaft having a smooth cylindrical portion that terminates as a pointed tip at the distal end and a helical threaded portion at the proximate end. A nut defining an aperture therethrough matingly threads along the helical threaded portion and the length of the deformable shaft is such as to permit the distal portion of the cylindrical portion to encircle the tooth and to loop above the shaft over a segment of the helical threaded portion. In an alternative embodiment, the longitudinal shaft has a detent at the proximate end and there are anchoring fixtures in the form of truncated conics which are adapted to travel along the shaft. One of the fixtures anchors in the detent and the other, is engaged against adjacent teeth by the nut, when the nut is turned down on the helical thread. The conics provide a bearing surface adapted to carry interconnecting elements such as wires or elastics for staplizing the jaw.

42 Claims, 4 Drawing Sheets

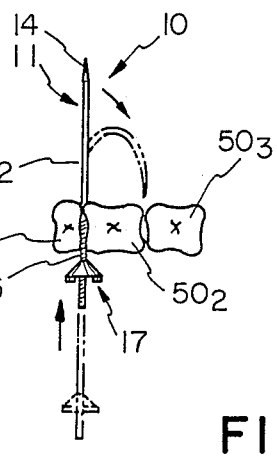
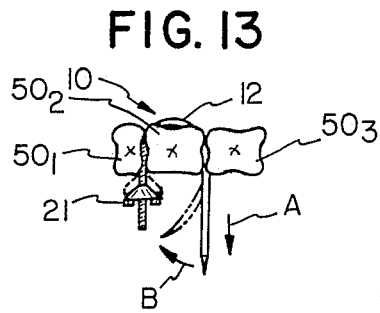
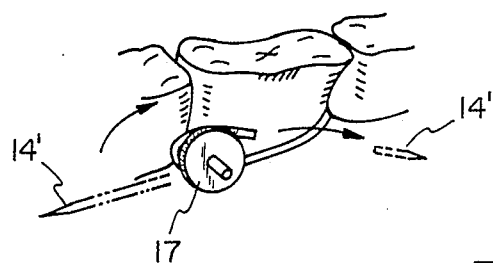
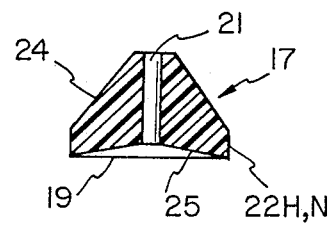
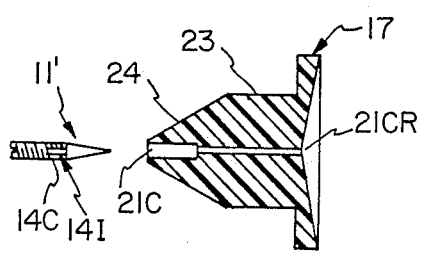
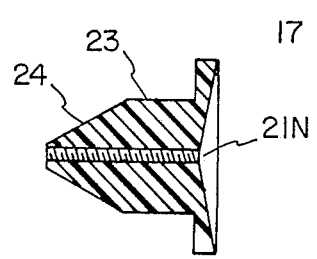

INTERDENTAL IMMOBILIZATION DEVICE

This invention relates to an interdental immobilization device.

From time to time, it is necessary to immobilize the human jaw.

This will be necessary when fractures of mandible occur or when (sparingly) one wishes to have their mouth fixed shut so as to avoid eating, and hence lose weight.

The existing method of the prior art uses a pliable metal strip with projecting hooks known as an archbar and several fine wires and rubber bands. The metal strip is secured tightly to the teeth of the upper jaw by passing a wire around the base of a tooth and through the gum and over each side of the tooth and also over the metal strip. At this point both ends of the wire are outside the mouth and are twisted together to hold the metal strip urgingly against the outside surface of the teeth. The twisted wire is then cut to a length of approximately ⅛ to ¼ inch and bent backward towards the gum and preferably placed in between two adjacent teeth to prevent irritation on the inside of the lips.

This is repeated spatially around eight to twelve teeth of the upper jaw and the same is repeated over the lower jaw.

The metal strip has the projecting hooks spatially disposed on its outside surface and over these hooks small rubber bands or wires are then attached between those hooks of the metal strip attached to the teeth of the lower jaw and those hooks of the upper jaw. This technique has been published at pages 301 through 303 in Surgery of the Upper Respiratory System (Vol 1-2nd Edition) by William W. Montgomery M.D., Published by Lea & Febiger, Copyright 1979.

This particular prior art technique, which is extremely common in North America, and around the world has several disadvantages. The most dominant disadvantage is that during twist tightening of the wires, the wires can easily snap and the whole process must be repeated hence adding to the length of the installation procedure. It is not uncommon for this procedure to take between 1 and 2 hours of operating theatre time since a general anesthetic for the patient is always needed.

After approximately two days of use, the wires need to be retightened and retwisted as they have a tendency to loosen off and sometimes break. If they break during tightening, the patient must be re-anesthetized again within the operating theatre and new wires inserted as before. Further, the patient must be anesthetized for wire removal after the jaw has mended.

With the recent scare of AIDS and HEPATITIS B, there is a constant danger of trauma to the surgeons hands from the ends of the wire and hence exposure to the patient's body fluids and blood since the passing of the wire between the teeth, always ruptures the gum and the gum bleeds.

The conceived fixtures according to the invention have several advantages over the prior art; namely, (a) anesthetic is generally required only on the installation of the fixture;

(b) the fixture may be tightened by the simple expedient of turning down a nut on a flexible screw as there is no wire twisting with these appendant possibilities of wire breakage and blood letting; thus, the prior art step for re-installation of broken wires in an operating theatre environment with the patient anesthetized is avoided; not to mention the associated blood letting; and, (c) the fixture is easily removed generally without the patient being re-anesthetized.

In one embodiment the invention is disclosed as a novel three part fixture, and in another embodiment it is a four part fixture; both of these embodiments employ frusto-conical surfaces or alternative truncated cones as a pair, or in combination with a nut and screw. These fixtures expose an anchoring surface associated with the nut, which preferably is cylindrical, onto which rubber bands or wires may be attached so as to fix the lower and upper jaw into rigid position.

In a third embodiment the interdental immobilization device is but a two part fixture, a yieldable stainless steel shaft with one end as a threaded helical shaft that extends into a smooth continuous shaft that then tapers into a pointed tip. The smooth cylindrical portion of the shaft is capable of being bent, and a threaded nut is adapted to threadingly mate onto the threaded shaft and to tighten down and to locate the shaft and nut in a clamping arrangement about a tooth in a manner as will be described.

In one variant of both embodiments of the nut, the nut defines a smooth bored channel sized slightly smaller in diameter than that of the threaded shaft. In this variant, the nut is composed of a plastic material such as nylon. As a further variant of the nut the channel has a shorter major bore with diameter larger than that of the threaded shaft that steps into a longer minor bore with diameter slightly smaller than that of the threaded shaft. The length of the minor bore is substantially greater than that of the major bore. As a further alternative variant of the nut, the nut may have a helically threaded channel of constant diameter which threadingly mates with the helical thread of the screw and is composed of a biologically inert metal such as surgical stainless steel.

In these embodiments it is preferred that the nut have a truncated cone portion with the channel intersecting the truncation, and wherein the truncated cone portion extends into a cylindrical piece bounded by a bearing surface such as a hexagon or knurl. In an embodiment of the threaded shaft, the shaft has means to index itself into one of the cones as well as to protrude beyond the cone as a bent tip so when fixed between the teeth the bent tip stands as a protrusion in the crevice defined by these adjacent teeth.

The invention therefore contemplates a two part fixture for interdental immobilization comprising;

a longitudinal deformable shaft defining a helical threaded portion that extends from one end and that transforms into a smooth cylindrical rod that terminates at a pointed distal end and a screw member defining a bore therethrough adapted to matingly thread with the helical threaded portion, the length of the deformable longitudinal shaft being such a to permit the distal portion of the cylindrical rod to encircle a tooth and to loop about the shaft over a segment of the helical threaded portion.

The longitudinal shaft is surgical stainless steel in the preferred diameter of 0.025" to 0.032" inches and the screw member is nylon and the aperture is a step bore which steps from a major bore to a minor bore, the minor bore having a diameter at least equal to the exterior diameter of the stainless steel shaft. In the preferred embodiment, the nylon nut has a frusto-conical surface that extends into a cylindrical bearing portion and defines means for turning such frusto-conical surface.

The invention also contemplates a multi-part fixture for interdental immobilization comprising:

an elongated member carrying near one end, a detent, and near the other opposite end, a threaded portion; a first anchor means adapted to engage the detent; a second anchor means defining a body portion and a bore and adapted to travel on the member, the body portion having a cross-sectional area traverse to the bore that in part, is smaller than at other axial locations along the body portion so as to accomodate and carry interconnecting elements such as wires or elastics.

More specifically, there is an "L" shaped helical shaft with a distal arm and a threaded shaft and a pointed tip thereon a proximate arm wherein the proximate arm extends through an obtuse angle into a straight inclined piece that acts as a protrusion. This shaft protrudes through an anchor member which in one embodiment is a truncated cone. The screw and cone are stainless steel in the preferred embodiment while the second anchor means, in the preferred embodiment includes a capture region and is composed of nylon with a smaller major bore stepping into a smaller minor bore sized a diameter smaller than that of the screw so that the screw can tap into the minor bore a helical thread for matingly securing the nut onto the screw. The screw also carries a capture region which in its preferred embodiment is a circumferential shoulder which acts as a bearing surface for interjoining a plurality of said fixtures located spatially between teeth of the upper and lower jaw.

The invention will now be described by way of example and reference to the accompanying drawings in which.

Figure 4:
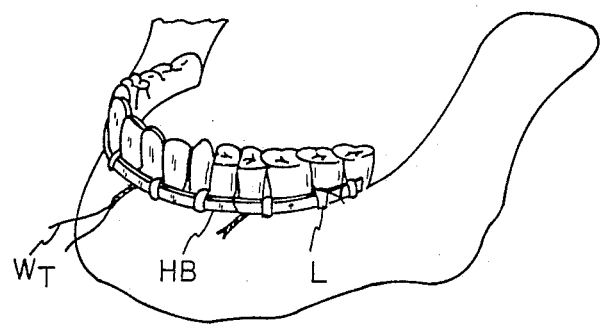
FIG. 4 is a perspective view of the first step according to the prior art.
Figure 7:
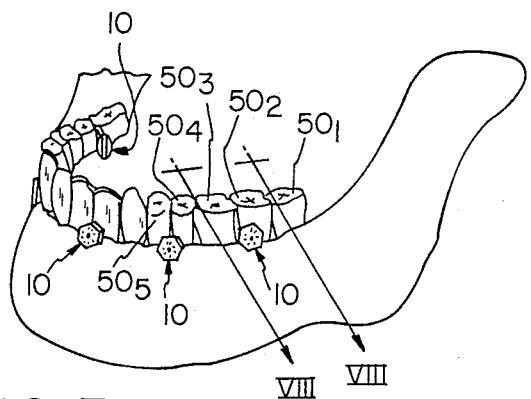

FIG. 7 corresponds to FIG. 4 as it relates to the implantation of devices according to the invention.

Figure 8:
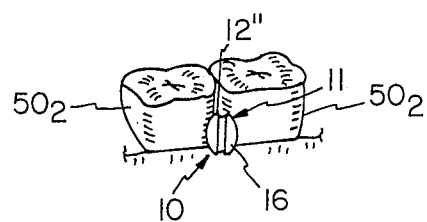

FIG. 8 is a perspective view showing the implantation of an embodiment of the invention between teeth as viewed from the inside of the mouth; and, hence is a view along VIII-VIII of FIG. 7.

Figure 9:
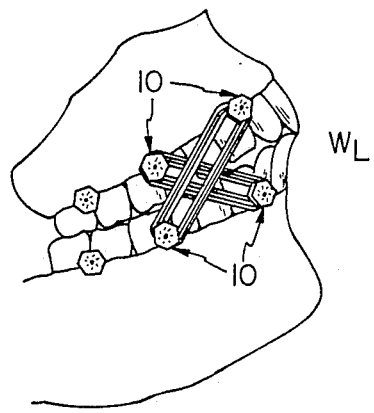

FIG. 9 is a partial perspective view of a jaw indicating the mode of securing the upper and lower jaws according to the invention.

FIG. 10 is cross-sectional view of one embodiment of the nut.

FIG. 11 is a cross-sectional view of another embodiment of nut according to the invention.

FIG. 12 is a top plan view of the two part device according to the invention shown during its initial stages of installation between two adjacent teeth.

FIG. 13 shows the second step of the installation procedure of the two part device where the smooth cylindrical portion of the shaft has been bent and pushed through the space between said one tooth and the next adjacent tooth.

FIG. 14 is a perspective view indicating the third step of the installation procedure of the two part device.

FIG. 15 is a cross section through an alternative nut having a smooth uniform bore.

Figure 1:
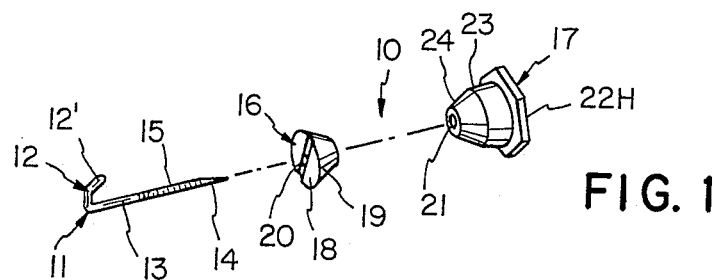
FIG. 1 is a perspective assembly view the three part embodiment of the invention.
Figure 2:
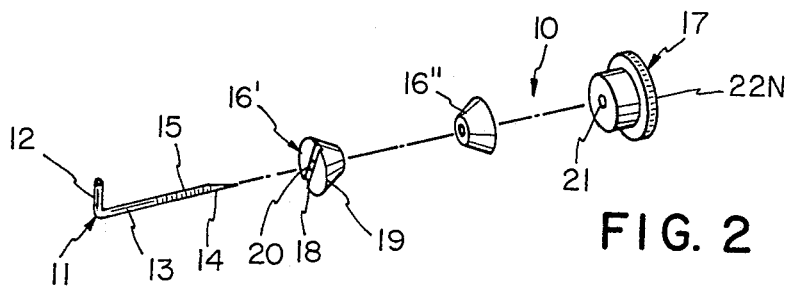
FIG. 2 is a perspective assembly view of the four part embodiment of the invention.

Referring to FIG. 1, the fixture 10, according to the invention, consists of a U shaped shaft 11 with an upstanding proximate arm 12 that is bent through an obtuse angle 12' to terminate as a forwardly inclined straight piece 12". From the promximate arm 12, it extends as a longitudinal shaft 13 with its distal end tapering to a point at 14. Part of the shaft 13 is helically threaded as at 15. A truncated conic member, or cone 16 consists of a flat bottom 19 through which extends a slot 20 and the cone defines therethrough a channel 18 which passes through the apex of the cone and hence truncates it as shown in FIGS. 1 and 2. The channel 18 is a diameter slightly larger than the diameter of the shaft 13 so as to allow free passage therethrough. This is more clearly seen in the sectional FIG. 3. The slot 20 is outwardly tapered at 20' at the identical obtuse angle as at 12' so that the proximate arm 12 may appropriately index within the slot 20 and the bend 12' and straight distal piece 12" mate against the inclined or bevelled surface of slot 20' allowing the end of the distal piece 12' to protrude into the crevice defined by the bodies of two adjacent teeth.

Figure 3:
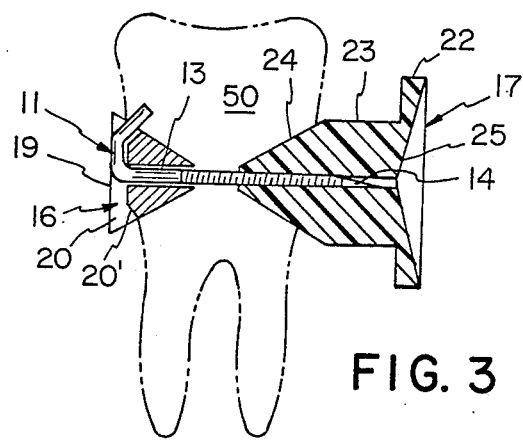
FIG. 3 is a section through the embodiment according to FIG. 1 showing its implantation adjacent a tooth shown in phantom.

The nut 17 in one of the preferred embodiments, that is shown in FIGS. 1 and 10, is formed of nylon and the channel 21 is a stepped smooth walled channel, as more clearly seen in FIG. 10, with a shorter major bore 21C and a longer minor bore 21CR; the major bore interfacing with the apex thereof. Also, the nut 17 may be profiled as seen in FIGS. 1 and 3 so as to provide an outer gripping surface 12, either a hexagonal gripping surface 22H sized greater than the diameter of the cylindrical shoulder 23 through which it steps into a truncated conical section 24, or as seen in FIG. 2, a knearl gripping surface 22 N. The face of the nut obverse to the truncated conic 24 is conically recessed at 25 as more clearly seen in FIG. 3 (see also FIGS. 10 and 11). If the tip 14 of the shaft 13 extends into the conical recess 25 after the physician has placed the fixture 10 between teeth, as will be disclosed hereafter, the physician has room to insert a pair of diagonal cutters 30 (see FIG. 3A), or the like, into the recess 25; and, to snip off the protruding segment of shaft 13 and the tip 14 which are collectively shown as SR so as not to cause abrasion to the inner skin of the mouth.

Referring to FIGS. 3 and 8, in application, the shaft 11 is fitted to slip through cone 16 with the proximate arm 12 indexing into the slot 20. The shaft 11 is pushed between the base of two adjacent teeth 50 ($50_2$ and $50_3$ in FIG. 8) and the point 14 assists in the penetration of the shaft 11 from the inside of the mouth through the gum mass between said teeth $50_2$ and $50_3$ to the outside gum surface. The nut 17 is then, if hexagonally formed as in FIG. 1, put into a socket wrench and threaded onto the shaft 11 so as to urge against the adjacent teeth $50_2$ and $50_3$ as well as the adjacent gum mass. If the profiled nut of FIG. 1 having the hexagonal surface 22H is nylon, and has the stepped bore channel, shown in FIG. 10, the tapered tip 14 of the screw 11 indexes into the opening face of the major channel 21C and as the nut is rotated, the shaft 11 itself taps a helical thread into the wall of the minor bore 21CR of the nylon nut of FIGS. 1, 3 and 10 and secure anchoring is thereby achieved. As the nut 17 is turned tighter, the cone 16 and the conic section 24 of the nut 17 are drawn toward each other and a tight fit is achieved. If there be any loosening off at a later time it is simple to just slightly turn down the nut with the socket wrench.

This step is repeated to locate, as shown in FIG. 7, a plurality of fixtures 10 mounted between teeth along the lower jaw. The steps are repeated in relation to the upper jaw.

The shoulder cylindrical surface 23 of the nut 17 is used as the capture region for anchoring wire W, which is laced between top and bottom fixtures as shown in FIG. 9. In this way, the lower jaw is immobilized to the upper jaw.

This wrapping may just be accommodated by weaving or wrapping of wire W or if preferred, elastic loops $W_1$ may be used.

Figure 5:
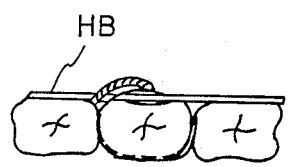
FIG. 5 is a plan view of the brace according to the prior art secured by wire to teeth.
Figure 6:
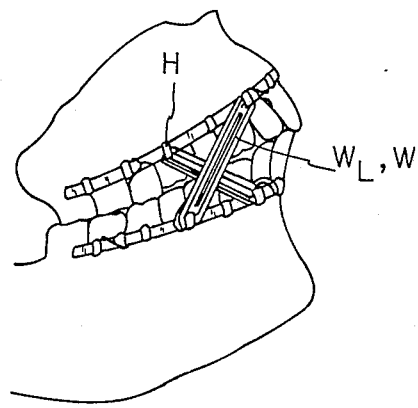
FIG. 6 illustrates the securing of the upper and lower jaw according to the prior art.

According to the prior art, and referring to FIG. 4 through 6, the elastic loops $W_1$ are wrapped over hooks H, spatially disposed along a flexible stainless steel arch bar HB which is placed at the gum line on the facial side of the teeth and secured there by wire $W_t$ which wrap around a single tooth and extend between adjacent teeth and are twisted over the front or facial portion of the arch bar, as more clearly seen in FIG. 4.

Referring to FIG. 2, a further alternative embodiment consists of two identical truncated stainless steel conics shown as 16' and 16". The shaft 11 has but a proximate straight arm 12 and that arm indexes into the slot 20 of the truncated conic 16'. The nut 17 is fashioned without a tapered conic section 24 and hence a flat bearing as shown and for reason, a second conic 16" identical to that of 16' is used as the bearing member for the nut. Similarly, as disclosed relative to FIG. 1, the shaft 11, the conics 16' and 16" and nut 17 may be installed between the teeth. This particular embodiment is less favourable to that of FIGS. 1 and 10 since there are 4 rather than 3 discrete components to consists of two identical truncated stainless steel conics shown as 16' and 16". The shaft 11 has but a proximate straight arm 12 and that arm indexes into the slot 20 of the truncated conic 1, a further alternative embodiment consists of two identical truncated stainless steel conics shown as 16' and 16". The shaft 11 has but a proximate straight arm 12 and that arm indexes into the slot 20 of the truncated conic 1 surface 24.

Figure 3A:
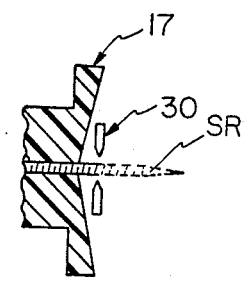
FIG. 3A is a partial section of a longer screw in the nut of FIG. 3 showing how the screw distal end is severed after implantation.

Referring to FIG. 3A the length of the shaft 11 may be structured quite long so as to accommodate various depths (thicknesses of teeth). In that instance, the tip 14 of the shaft 11 protrudes well beyond the face of the conical recess 25 of the nut as shown in FIGS. 3 and 3A. This overhang extent SR may be cut off with a pair of wire cutters 30 as shown in FIG. 3A. This provides means for reducing the length of the screw each time that the nut 17 is turned down on the teeth to tighten the fixture. Abrasion to the inner lip and cheek is thus avoided.

Returning now to FIG. 10, when the nut is composed of nylon, the channel may be a two step bore as shown that is a shorter major bore 21C that steps into a longer minor bore 21 CR. The thread 15 of the shaft 11 may be modified (though not required) near its tip 14 with a cup at 14C and a protruding piece 14I which cooperatively act as a "tap". When the nylon nut 10 is turned down on this end taped threaded shaft of the shaft 11' the shaft 11' self taps the minor bore 21CR to form a mating thread therein securing the nut 17 thereon.

In the preferred embodiment of FIGS. 1, 3, and 10, the shaft 11, and cone 16, are stainless steel and the nut 17 is made of nylon. We have found that a cone base diameter of approximately 5 m.m. and a cone height of 3 m.m. is satisfactory with an angle of 40°. This means that the hexagon diameter 22H of the nut 17 is preferrably about 7 m.m.; while the shoulder portion 23 diameter is about 5 m.m. with a depth of shoulder of about 2 m.m. to allow adequate space for winding of wire or elastics $W_1$ between respective shoulders of fixtures in a manner as seen in FIG. 9. In this respect the preferred length of the shaft is about 12 m.m. with the shaft arm 12 having a length of approximately 2.5 m.m. and protrusion 12" of about 2.5 m.m. and an outside bend diameter at 12' of 0.8 m.m. In this respect, slot 20 cut into the face of the base of the cone has a preferred depth of approximately 1 m.m. and a preferred width of between 0.8 and 1 m.m.

In a variant of the nut 17, it may be stainless steel as shown in FIGS. 1 and 11. In this instance, the central channel 21 is a uniform helically threaded channel 21N shown in FIG. 10. The stainless steel nut may be profiled with either the hexagonal surface 22H of FIG. 1 or with a cylindrical knurled surface 22N and of FIG. 2.

It should be noted, that if the formed shaft 11 of FIG. 1 is used, the proximate arm tip of the straight piece 12" protrudes beyond the conic 16 (as shown in FIG. 3) into the crevice defined by the bodies of two adjacent teeth (see FIG. 8) and anchors the screw preventing its rotation and the corresponding rotation of the conic 16 in FIGS. 1, 3, and 8, as the nut 17 is initially turned down. If the shaft 11 is of the unmodified shape, as shown in FIG. 2, the screw 11 and the conic 16' of that finger has a tendency to rotate on the initial turning down of the nut 17 irrespective of which profile 22H or 22N the nut has. This impediment is amplified when the step bore nylon nut of FIG. 10 is used on the screw 11 of FIG. 2, or FIG. 10, while if the stainless steel nut 17 of FIG. 11 is used, i.e., having a uniform threaded channel 21N, the problem is less pronounced.

Referring to FIG. 12, the two part interdental device is generally shown as 10; and, consists of a shaft 11 that includes a longitudinal smooth portion 12 which tapers into a point or tip 14 at one end and extends into a helical thread portion 15 at the other end. The shaft member has a length of approximately 3 inches with the helical thread portion length of about ⅜ of an inch and is made of surgical stainless steel with a preferred diameter range of 0.025" (22 gauge) to 0.032" (20 gauge). A nut 17 is formed of nylon such as a Nylon Polyamide. Particularly suitable is a Nylon Polyamide pipe 6—6 available from Cadilac Plastics of Toronto, Ontario, Canada; this particular nylon will withstand temperatures of approximately 200° F., and remain rigid and hence can be easy autoclaved. Its melting temperature is about 400° F. It also has a Rockwell hardness of R110-R120. The nut 17, has a channel 21 therethrough, preferably as a smooth bore as shown in FIG. 15. The nut 17 then can be threaded onto the threaded shaft 15 part way down as shown in FIG. 12, and delivered to the surgeon this way.

Referring to FIG. 7, successive adjacent teeth $50_1$, $50_2$, $50_3$ and $50_4$, are shown referenced while the lower jaw is illustratively shown.

In order to immobilize one's jaw, while the patient is anesthitized, the device 10 is pushed between the adjacent teeth $50_1$ and $50_2$ as shown in FIG. 12, and then, with a pair of pliers, the tip 14 is bent into the phantom position and thereafter pushed between the next adjacent teeth $50_2$ and $50_3$ so as to extend in the fashion of FIG. 13. The tip 14 is pulled taut, with a pair of pliers, in the direction of the arrow A so that the shaft 12 fits snug about the back of the tooth $50_2$ and with the truncated conical surface 20 of the nut 17 resting snug against adjacent teeth $50_1$ and $50_2$, as shown in phantom in FIG. 13. The tip 14 is then moved with tweezers in the direction of arrow B and hence into the phantom position; and, then eventually wrapped about the segment of the helical shaft 15, disposed between nut 17 and the adjacent teeth $50_1$ and $50_2$, in the fashion shown in FIG. 14. The distal end or tip 14 of the shaft 12 (the phantom portion referred to as 14' in FIG. 14) is cut away with a pair of wire cutters and discarded. Thereafter, the nut 15 is turned down snug on the helical thread to tighten the device 10 and to anchor it about the tooth $50_2$ as shown in FIG. 3. Any excess helical thread 14 that protrudes into the truncated conical recess 25 of the nut 17 be removed with wire cutters. Any exposed ends of the shaft 11 are therefore removed and no scratching or other abrasion takes place in the mouth of the wearer when implanted. There is virtually no blood letting.

We claim:

1. A two part fixture adapted to act as an anchoring means in an interdental immobilization procedure comprising;
(a) a longitudinal deformable shaft defining a helical threaded portion that extends from one end and that transforms into a smooth cylindrical rod that terminates at a pointed distal end; and,
(b) a screw member defining a bore therethrough adapted to matingly thread with the helical threaded portion, the length of the deformable longitudinal shaft being such as to permit the distal portion of the cylindrical rod to encircle a tooth and to loop about the shaft over a segment of the helical threaded portion.

2. The fixture as claimed in claim 1, wherein the screw member is profiled as a conic.

3. The fixture as claimed in claim 2, wherein the conic is frusto-conical.

4. The two part fixture as claimed in claim 3 wherein the nut is nylon and the elongated screw member is stainless steel.

5. The two part fixture as claimed in claim 3, wherein the elongated screw member is stainless steel of a diameter in the range of 0.025" to 0.032" and the nut is nylon.

6. The two part fixture as claimed in claim 3, wherein the elongated screw member is stainless steel of a diameter in the range of 0.025" to 0.032" and the nut is nylon, and the profile of the nut is a hexagon.

7. The fixture as claimed in claim 3, wherein the elongated screw member is 3" long.

8. The two part fixture as claimed in claim 3, wherein the elongated screw member is stainless steel and of a diameter in the range of 0.025" to 0.032" the nut is nylon and the aperture is a smooth continuous bore, sized to at least the root threaded diameter of the helical threaded portion.

9. The two part fixture as claimed in claim 3, wherein the elongated screw member is stainless steel and of a diameter in the range of 0.025" to 0.032" the nut is nylon and the aperture is a two step bore, a major bore sized to at least the diameter of the elongated screw member, and a minor bore sized to at least the root thread diameter of the helical threaded portion.

10. The fixture as claimed in claim 3, wherein the helical thread is a thread selected from the group of threads comprising a buttress form thread and a full depth V shaped thread.

11. The fixture as claimed in claim 3, wherein the shaft is surgical stainless steel and the screw member is a nylon polyamide.

12. The fixture as claimed in claim 3, wherein the shaft is surgical stainless steel and the screw member is a nylon polyamide wherein, the nylon polyamide has a Rockwell hardness of R110 to R120.

13. A two part fixture as claimed in claim 2 wherein the nut is nylon and the elongated screw member is stainless steel.

14. A two part fixture as claimed in claim 2 wherein the elongated screw member is stainless steel of a diameter in the range of 0.025" to 0.032" and the nut is nylon.

15. The two part fixture as claimed in claim 2, wherein the elongated screw member is stainless steel of a diameter in the range of 0.025" to 0.032" and the nut is nylon, and the profile of the nut is a hexagon.

16. The fixture as claimed in claim 2, wherein the elongated screw member is 3" long.

17. The two part fixture as claimed in claim 2, wherein the elongated screw member is stainless steel and of a diameter in the range of 0.025" to 0.032" the nut is nylon and the aperture is a smooth continuous bore, sized to at least the root thread diameter of the helical threaded portion.

18. The two part fixture as claimed in claim 2, wherein the elongated screw member is stainless steel and of a diameter in the range of 0.025" to 0.032" nut is nylon and the aperture is a two step bore, a major bore sized to at least the diameter of the elongated screw member, and a minor bore sized to at least the root thread diameter of the helical threaded portion.

19. The fixture as claimed in claim 2, wherein the helical thread is a thread selected from the group of threads comprising a buttress form thread and a full depth V shaped thread.

20. The fixture as claimed in claim 2, wherein the shaft is surgical stainless steel and the screw member is a nylon polyamide.

21. The fixture as claimed in claim 2, wherein the shaft is surgical stainless steel and the screw member is a nylon polyamide wherein, the nylon polyamide has a Rockwell hardness of R110 to R120.

22. The two part fixture as claimed in claim 1, wherein the nut is nylon and the elongated screw member is stainless steel.

23. The two part fixture as claimed in claim 1 wherein the elongated screw member is stainless steel of a diameter in the range of 0.025" to 0.032" and the nut is nylon.

24. The two part fixture as claimed in claim 1, wherein the elongated screw member is stainless steel of a diameter in the range of 0.025" to 0.032" and the nut is nylon, and the profile of the nut is a hexagon.

25. The fixture as claimed in claim 1, wherein the elongated screw member is 3" long.

26. The two part fixture as claimed in claim 1, wherein the elongated screw member is stainless steel and of a diameter in the range of 0.025" to 0.032" the nut is nylon and the aperture is a smooth continuous bore, sized to at least the root thread diameter of the helical threaded portion.

27. The two part fixture as claimed in claim 1, wherein the elongated screw member is stainless steel and of a diameter in the range of 0.025" to 0.032" the nut is nylon and the aperture is a two step bore, a major bore sized to at least the diameter of the elongated screw member, and a minor bore sized to at least the root thread diameter of the helical threaded portion.

28. The fixture as claimed in claim 1, wherein the helical thread is a thread selected from the group of threads comprising a buttress form thread and a full depth of V shaped thread.

29. The fixture as claimed in claim 1, wherein the shaft is surgical stainless steel and the screw member is a nylon polyamide.

30. The fixture as claimed in claim 1, wherein the shaft is surgical stainless steel and the screw member is a nylon polyamide wherein, the nylon polyamide has a Rockwell hardness of R110 to R120.

31. A fixture for interdental immobilization comprising:
(a) an elongated screw member carrying near one end, a detent, and near the other opposite end, a threaded portion;
(b) a first anchor means adapted to engage the detent; and,
(c) a second anchor means defining a body portion and a bore and adapted to travel on the screw member, the body portion having a cross-sectional area traverse to the bore that in part, is smaller than at other axial locations along the body portion so as to accomodate and carry interconnecting elements such as wires or elastics.

32. The fixture as claimed in claim 31 wherein the interconnecting engagement member is a threaded shaft and said first anchor member is a truncated conic defining a channel through which said shaft extends and wherein said second anchor means is integral with said adjustably locating means (c) and includes means for engagement with said shaft whereby to position said first and second anchor means relative to each other.

33. The fixture as claimed in claim 32 wherein said means (c) for locating includes a bearing surface adapted to locate said means (c) and said bearing anchor means relative to said first anchor means.

34. The fixture as claimed in claim 31 wherein the detent is in the form of an L.

35. The fixture as claimed in claim 34, wherein the elongated screw member is "L" shaped having a distal arm with a threaded shaft and pointed tip thereon and a proximate arm.

36. The fixture as claimed in claim 34, wherein the elongated screw member is "L" shaped having a distal arm with a threaded shaft and pointed tip thereon and a proximate arm thus extends through an obtuse angle into a straight inclined piece that acts as a protrusion.

37. The fixture as claimed in claim 31 wherein the first anchor means has a slot for engagement with the detent.

38. The fixture as claimed in claim 37, wherein the elongated screw member is "L" shaped having a distal arm with a threaded shaft and pointed tip thereon and a proximate arm thus extends through an obtuse angle into a straight inclined piece that acts as a protrusion.

39. The fixture as claimed in claim 37 wherein the bore of the second anchor means is adapted to threadingly mate with and travel along the threaded portion.

40. The fixture as claimed in claim 39, wherein the elongated screw member is "L" shaped having a distal arm with a threaded shaft and pointed tip thereon and a proximate arm thus extends through an obtuse angle into a straight inclined piece that acts as a protrusion.

41. The fixture as claimed in claim 31 wherein the bore of the second anchor means is adapted to threadingly mate with and travel along the threaded portion.

42. The fixture as claimed in claim 41, wherein the elongated screw member is "L" shaped having a distal arm with a threaded shaft and pointed tip thereon and a proximate arm thus extends through an obtuse angle into a straight inclined piece that acts as a protrusion.

* * * * *